(12) United States Patent
Mercer et al.

(10) Patent No.: US 8,896,439 B2
(45) Date of Patent: Nov. 25, 2014

(54) REMOTE MAINTENANCE OF MEDICAL IMAGING DEVICES

(75) Inventors: Michael J. Mercer, Woodstock, IL (US); G. Wayne Moore, Lyons, CO (US); James Gessert, Loveland, CO (US)

(73) Assignee: Consensys Imaging Service, Inc., Cary, IL (US)

(*) Notice: Subject to any disclaimer, the term of this patent is extended or adjusted under 35 U.S.C. 154(b) by 732 days.

(21) Appl. No.: 12/951,841

(22) Filed: Nov. 22, 2010

(65) Prior Publication Data

US 2011/0121969 A1 May 26, 2011

Related U.S. Application Data

(60) Provisional application No. 61/264,544, filed on Nov. 25, 2009.

(51) Int. Cl.
*G08B 1/08* (2006.01)

(52) U.S. Cl.
USPC .............. 340/539.12; 340/286.07; 340/573.1; 705/2

(58) Field of Classification Search
USPC ............... 340/540, 539.12, 573.1, 286.07; 600/407, 409, 437, 447, 300, 301; 702/182, 184; 705/2, 3, 52, 56
See application file for complete search history.

(56) References Cited

U.S. PATENT DOCUMENTS

| | | | |
|---|---|---|---|
| 6,377,162 B1* | 4/2002 | Delestienne et al. | .... 340/286.07 |
| 6,920,776 B2 | 7/2005 | Gessert et al. | |
| 6,928,856 B2 | 8/2005 | Gessert et al. | |
| 7,007,539 B2 | 3/2006 | Gessert et al. | |
| 7,035,768 B2* | 4/2006 | Matsuda | ........................ 702/184 |
| 7,155,957 B2 | 1/2007 | Gessert et al. | |
| 7,208,529 B2 | 4/2007 | Crews | |
| 7,244,230 B2 | 7/2007 | Duggirala et al. | |
| 7,278,289 B2 | 10/2007 | Gessert et al. | |
| 7,418,480 B2* | 8/2008 | Katsman et al. | ............... 709/217 |
| 8,125,311 B2* | 2/2012 | Takimoto et al. | .............. 340/5.2 |
| 2003/0097054 A1 | 5/2003 | Sasaki et al. | |
| 2005/0084060 A1 | 4/2005 | Seppi et al. | |
| 2008/0162393 A1 | 7/2008 | Iliff | |
| 2008/0173089 A1 | 7/2008 | Wright et al. | |
| 2010/0332245 A1* | 12/2010 | Choubey et al. | ................... 705/2 |

OTHER PUBLICATIONS

Applicant: Unisyn Medical Technologies, Inc. Notification of Transmittal of the International Search Report and the Written Opinion of the International Searching Authority, or the Declaration. International Application No. PCT/US2010/057876. International Filing Date Nov. 23, 2010.

* cited by examiner

*Primary Examiner* — Hung T. Nguyen
(74) *Attorney, Agent, or Firm* — Kory D. Christensen; Stoel Rives LLP

(57) ABSTRACT

A medical imaging device that uses electromagnetic or acoustic information to generate a patient image is remotely maintained. A set of operational characteristics for the device is maintained by a maintenance system disposed remotely from the device. Data from sensors disposed local to the device are received over a network at the maintenance system. A set of parameter measures is derived from the received data and analyzed in comparison with the set of operational characteristics to identify a predicted malfunction of a component of the device. The maintenance system is thus able to initiate a repair of the medical imaging device by generating an alert in response to identification of the predicted malfunction.

22 Claims, 4 Drawing Sheets

REMOTE MAINTENANCE OF MEDICAL IMAGING DEVICES

CROSS REFERENCE TO RELATED APPLICATION

This application is a nonprovisional of, and claims the benefit of the filing date of, U.S. Prov. Pat. Appl. No. 61/264,544, entitled "SYSTEM AND METHOD FOR INTEGRATED REMOTE MONITORING AND SERVICE OF MEDICAL IMAGING DEVICES," filed Nov. 25, 2009 by Michael J. Mercer et al., the entire disclosure of which is incorporated herein by reference for all purposes.

BACKGROUND OF THE INVENTION

This application relates generally to medical imaging devices. More specifically, this application relates to systems and methods for remote maintenance of medical imaging devices.

Modern medical imaging systems may be broadly said to rely on a single umbrella concept that is implemented in a variety of different ways with a number of different kinds of systems: radiation is propagated into the tissue of a patient, received after it scatters within the tissue, and used to reconstruct an image of interior structure so that a physician can make a diagnosis. The most common forms of radiation used are electromagnetic and acoustic. Electromagnetic radiation is used in such devices as traditional X-ray machines that produce projection radiographs, computed tomography ("CT") and computed axial tomograph ("CAT") machines that produce tomograms, mammography devices that produce mammograms, and others. These techniques may at times be used with substances delivered to the patient, particularly radioisotopes that emit markers that can be imaged and used in functional studies. Magnetic-resonance imaging ("MRI") uses the creation of a magnetic field in which a patient rests so that when radio waves are pulsed into tissue they cause hydrogen atoms to resonate, releasing energy that can be used for imaging. These techniques are especially useful in imaging soft tissues in the body, and radio waves have a sufficiently long wavelength that, unlike techniques that use higher energy radiation, they are nonionizing.

Acoustic radiation, which is also nonionizing, is also used in a variety of different ways, usually through some form of ultrasonography in which acoustic waves in the megahertz range are delivered to tissue. Variants include the use of B scans, the use of Doppler effects in the imaging of bloodflow, and the use of techniques to generate three-dimensional images. In some cases, imaging is achieved through a combined use of acoustic and electromagnetic techniques, exploiting advantages from both types of techniques to increase the useful diagnostic information that is collected.

Still other imaging methods are used in other specialized applications. For example, thermographic techniques may be used to detect infrared radiation emanating from the body in the form of heat, with variations in the heat distribution providing diagnostic imaging information.

Accurate diagnosis by physicians depends critically on the proper functioning of the device used to deliver the different forms of radiation. Although the different kinds of medical imaging devices have particular designs and properties, all of them have a number of different components that interact in forming the irradiating field and in detecting the radiation emanating from the patient's body to generate an image. It is possible for the devices to function even if some component is malfunctioning, but the quality of the information may be degraded as a result of the malfunction.

Detection of malfunctions is thus a nontrivial task and most manufacturers of medical imaging devices include some diagnostic features in an effort to identify inoperable or malfunctioning components. These diagnostic features are inherently limited, providing an evaluation only of a portion of the total functionality of the devices. Moreover, when a malfunction is identified, there can be considerable downtime for the device while it undergoes evaluation to identify the specific cause of the malfunction and while repairs are effected, potentially interfering with scheduled medical procedures.

There is thus a general need in the art for early and reliable monitoring and maintenance of medical imaging devices.

SUMMARY

Embodiments of the invention provide methods and systems for remotely maintaining a medical imaging device. Such devices may generally be adapted to use electromagnetic or acoustic information to generate an image of at least a portion of a body of a patient.

Methods of the invention may include maintaining a set of operational characteristics for the medical imaging device. Such a set is maintained by a maintenance system disposed remotely from the medical imaging device. Data from a plurality of sensors disposed local to the medical imaging device are received over a network at the maintenance system. A set of parameter measures is derived from the received data and analyzed in comparison with the set of operational characteristics to identify a predicted malfunction of a component of the medical imaging device. The maintenance system is thus able to initiate a repair of the medical imaging device by generating an alert in response to identification of the predicted malfunction.

Different embodiments of the invention accommodate different types of sensors. For instance, in some cases, at least one of the plurality of sensors comprises a diagnostic sensor provided as part of the medical imaging device by a manufacturer of the medical imaging device, with at least another of the plurality of sensors comprising a sensor provided separately from the medical imaging device. In another embodiment, at least one of the plurality of sensors collects data associated with a characteristic of an environment within which the medical imaging device is disposed.

In a particular embodiment, at least one of the plurality of sensors collects data defining a diagnostic field pattern for an electromagnetic or acoustic field generated by the medical imaging device. The derived parameter measures are analyzed to identify an anomaly within the diagnostic field pattern.

In another particular embodiment, at least one of the sensors comprises a microphone and the set of parameter measures comprises an acoustic signature of nondiagnostic sounds generated by the medical imaging device. The derived parameter measures are analyzed to identify an anomaly in the acoustic signature.

Embodiments of the invention also accommodate a variety of ways to perform the analysis of the derived parameter measures. For example, the derived parameter measures may be analyzed by comparing each of the derived parameter measures with a respective normal operating range maintained as part of the set of operational characteristics. If each of the derived parameter measures is within the respective normal operating range, the analysis may proceed further by identifying the predicted malfunction from a combination of the derived parameter measures.

The medical imaging device may be one of a plurality of medical imaging devices disposed remotely from the maintenance system and in communication with the maintenance system.

The maintenance system may also be adaptive to the repairs. Specifically, in one embodiment, data related to the repair of the medical imaging device is received at the maintenance system, which updates the set of operational characteristics in response to the data related to the repair of the medical imaging device.

In other implementations, a connection is established with the medical imaging device with the maintenance system such that a technician may remotely effect changes in the medical imaging device by directing instructions through the maintenance system. Such instructions may effect a system reboot of the medical imaging device or may download a software update to the medical imaging device.

Embodiments of the invention may also be used with a variety of types of medical imaging devices having different operational designs, including devices made by different manufacturers. For example, in one embodiment, the medical imaging device comprises a first medical imaging device manufactured by a first manufacturer and a second set of operational characteristics are maintained for a second medical imaging device that is also adapted to use electromagnetic or acoustic information to generate an image of at least a portion of a body of a second patient. The second medical imaging device is manufactured by a second manufacturer distinct from the first manufacturer and has, at least in part, a design different from a design of the first medical imaging device. The steps of receiving data, deriving parameter measures, analyzing the parameter measures to identify a predicted malfunction, and initiating a repair may all be performed with the maintenance system for the second medical imaging device in addition to being performed for the first medical imaging device.

The various methods of the invention may also be embodied with a maintenance system that comprises a storage device, a communications device, and a processor connected with the storage device and with the communications device. The storage device is configured to maintain the operational characteristics for the medical imaging device and the communications device is configured to permit exchange of data with the plurality of sensors and with the medical imaging device, while the processor includes instructions to implement the methods as described above.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components. In some instances, a sublabel is associated with a reference numeral following a hyphen to denote one of multiple similar components. When reference is made to a reference numeral without specification to an existing sublabel, it is intended to refer to all such multiple similar components.

DETAILED DESCRIPTION OF EXEMPLARY EMBODIMENTS

Overview

Embodiments of the invention provide methods and systems for remote maintenance of medical imaging devices. As used herein, a "medical imaging device" is any device that uses a radiation field to create image representations of an interior portion of a human or animal body. Such radiation fields may include ionizing or nonionizing radiation, and may include combinations of ionizing and nonionizing radiation in different embodiments. In some instances, the medical imaging device both creates an incident radiation field that is directed at a human or animal patient and receives a scattered radiation field, but this is not required by the invention. In alternative embodiments, the device may be configured only for receipt of the scattered radiation field, with the incident radiation being created by another device or by using a radiation field created by a natural source.

Merely by way of illustration, examples of medical imaging devices include projection-radiograph X-ray devices; computed-tomography devices, including computed-axial tomography devices and single-photon-emission computed-tomography devices; positron-emission tomography devices; mammography devices; magnetic-resonance-imaging devices, including those equipped for functional magnetic-resonance imaging; scintiscanner devices; A-scan, B-scan, and other ultrasound devices; and others. As will be readily appreciated by those of skill in the art, different types of devices may include different types of components. Magnets, for example, are needed by magnetic-resonance imaging devices, but are not needed by some of the other devices. Magnetic-resonance devices also typically have cooling requirements that make use of liquid helium as a coolant that are not shared by some of the other devices. Ultrasound devices typically have a large number of probes, each of which may be at risk for malfunction. Furthermore, each of these different kinds of devices may be more or less sensitive to different kinds of variations in environmental conditions in which the devices operate.

Embodiments of the invention provide cost-efficient and effective maintenance of medical imaging equipment, potentially at a large number of remote equipment installation sites. Early warning of environmental changes at those sites, particularly changes that may affect the safe use of the device for an operator of the device or for a patient. This is achieved with an integrated system capable of remote access of the medical imaging device itself, of sensors that are disposed to monitor a state of the medical imaging device, and/or of sensors disposed to monitor the environment in which the medical imaging device operates. Furthermore, the maintenance system may incorporate learning mechanisms that continually refine the criteria by which potential malfunctions are identified, including predictive capability that allows for early warnings that can advantageously minimize the impact of repair downtime.

Figure 1:
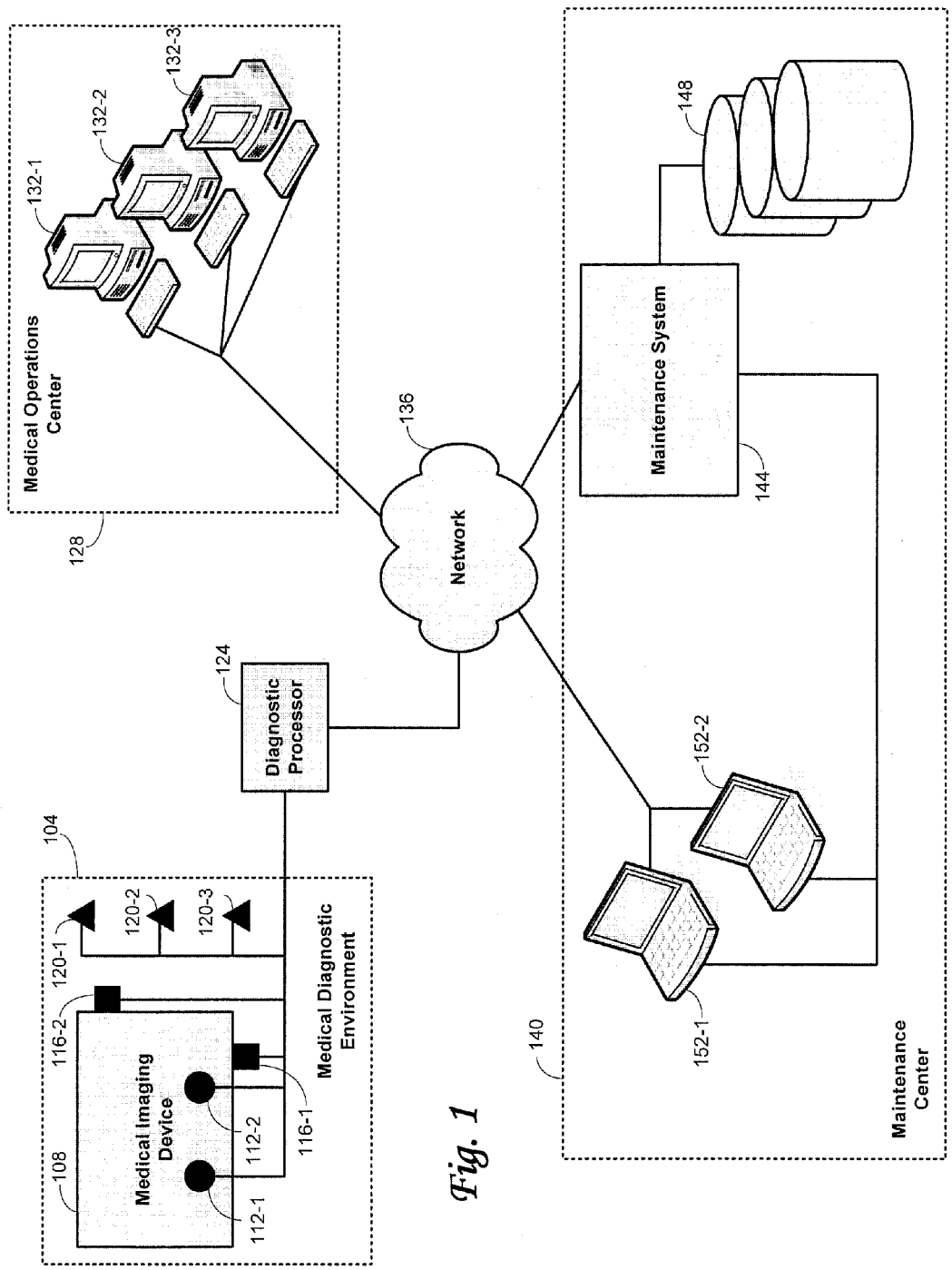
FIG. 1 provides a schematic illustration of systems that may be used in providing remote monitoring of medical imaging devices.

An overview of a system that may be used in providing remote maintenance of medical imaging devices is illustrated with the schematic diagram of FIG. 1. In this illustration, the medical imaging device 108 operates within a medical diagnostic environment 104, which may be a room in a hospital, clinic, physician's office, or the like. While it is generally expected that the medical imaging device 108 is substantially resident in a practical medical diagnostic environment 104, this is not a requirement of the invention, and in alternative embodiments the medical imaging device 108 may be moved among different environments 104. In such embodiments, separate information may be stored for each of the environments 104 where the medical imaging device 108 operates as described below.

Different kinds of data-collection sensors are indicated schematically with different shapes: circles 112 represent self-diagnostic sensors within the medical imaging device 108 itself, usually provided by the manufacturer of the medical imaging device 108 for executing self-diagnostic routines; squares 116 represent later-deployed sensors configured to monitor a parameter or characteristic of the medical imaging device 108 itself, usually provided by a party operating the maintenance system; and triangles 120 represent sensors deployed for monitoring environmental conditions of the medical diagnostic environment 104. Examples of each of these different types of sensors, all of which may potentially be accessed by the maintenance system in different embodiments is provided below. Collection of data by the different sensors 112, 116, and 120 may be coordinated locally to the medical diagnostic environment 104 with a diagnostic processor 124. The collected data may be assembled into log files that record the value of different measured parameters at different times, into error files that record the presence of an identified error in one of the sensors 112, 116, or 120 at particular times, and the like.

The diagnostic processor 124 may advantageously be configured to provided two-way information. Specifically, in addition to being configured to collect data from the sensors 112, 116, and 120, it may be configured to provide operational information to the sensors or to an operating system of the medical image device 108. Such operational information could take the form, for example, of providing software updates, of downloading new diagnostic routines, of downloading new diagnostic data, and the like. In addition, the two-way access of the diagnostic processor 124 permits real-time remote access of the operating system of the medical imaging device 108 in evaluating actual or predicted malfunctions as described below. In some configurations, such access may be complete, permitting a remote technician to perform the same operations with the medical imaging device 108 in providing maintenance as a local technician.

Maintenance functions are coordinated by the maintenance system 144, which may be located remote from a plurality of medical diagnostic environments 104 that contain medical imaging devices 108 being maintained. The maintenance system 144 communicates through a network 136 with the local diagnostic processor 124 in providing maintenance functions. In different embodiments, the network 136 may comprise a private network or may comprise a public network such as the Internet. A database or set of databases 148 in communication with the maintenance system store information related to the maintenance functions, such as log files, error files, and the like.

Such files may be organized in a variety of ways so that information can be extracted in aiding the identification of malfunctions. For example, data may be maintained for all medical imaging devices 108 of the same operational type, and this information may be further organized according to specific manufacturers, specific model numbers, specific histories of malfunctions, and the like. The information may also be organized according to specific types of medical diagnostic environments, providing a better basis for noting parameter values for devices in such environments that are suggestive of a malfunction.

The maintenance system 144 may be operated at a maintenance center 140 having one or more stations 152 that allow service technicians to access information through the maintenance system 144 and to access medical imaging devices 108 through the connections that have been described to perform maintenance functions.

In some embodiments, information collected by the diagnostic processor 124 may also be accessible at a medical operations center 128 that also has one or more stations from which access may be made. Such a medical operations center 128 could, for example, be an office of a hospital or clinic that contains the medical diagnostic environment 104 or could be a centralized facility for an organization that manages multiple hospitals or clinics, providing the hospital or organization with real-time access to parameter information about the medical imaging device 108.

The structural arrangement depicted in FIG. 1 is advantageously independent of specific structures or designs for the medical imaging devices 108, and may accommodate a variety of different types of structures and designs. In some embodiments, for example, the maintenance system 144 may be used in monitoring medical imaging devices 108 that are deployed in a geographically disparate way and that make use of different kinds of devices produced by different manufacturers. Merely by way of example, the same maintenance system 144 might be used in monitoring mammogram, ultrasound, and CAT-scan equipment at a particular medical facility. It might also be used in monitoring a variety of different ultrasound devices that perform similar functions but that are produced by different ultrasound-device manufacturers. These variety of devices might be located at a single medical facility or might be located at multiple medical facilities operated either by a single entity or operated by multiple unrelated entities.

This versatility is achieved in embodiments of the invention by implementing a consistent methodology for monitoring medical imaging devices as described in detail below. Such a methodology allows for different kinds of data as may be generated by the various devices themselves and allows for different formats in which the data are produced. Versatility is also achieved by tailoring the types of sensors deployed so that information most relevant to particular devices, particular manufacturers, particular environments, and the like are accommodated. Several examples of sensors that may be used in different embodiments are described below.

Figure 2:
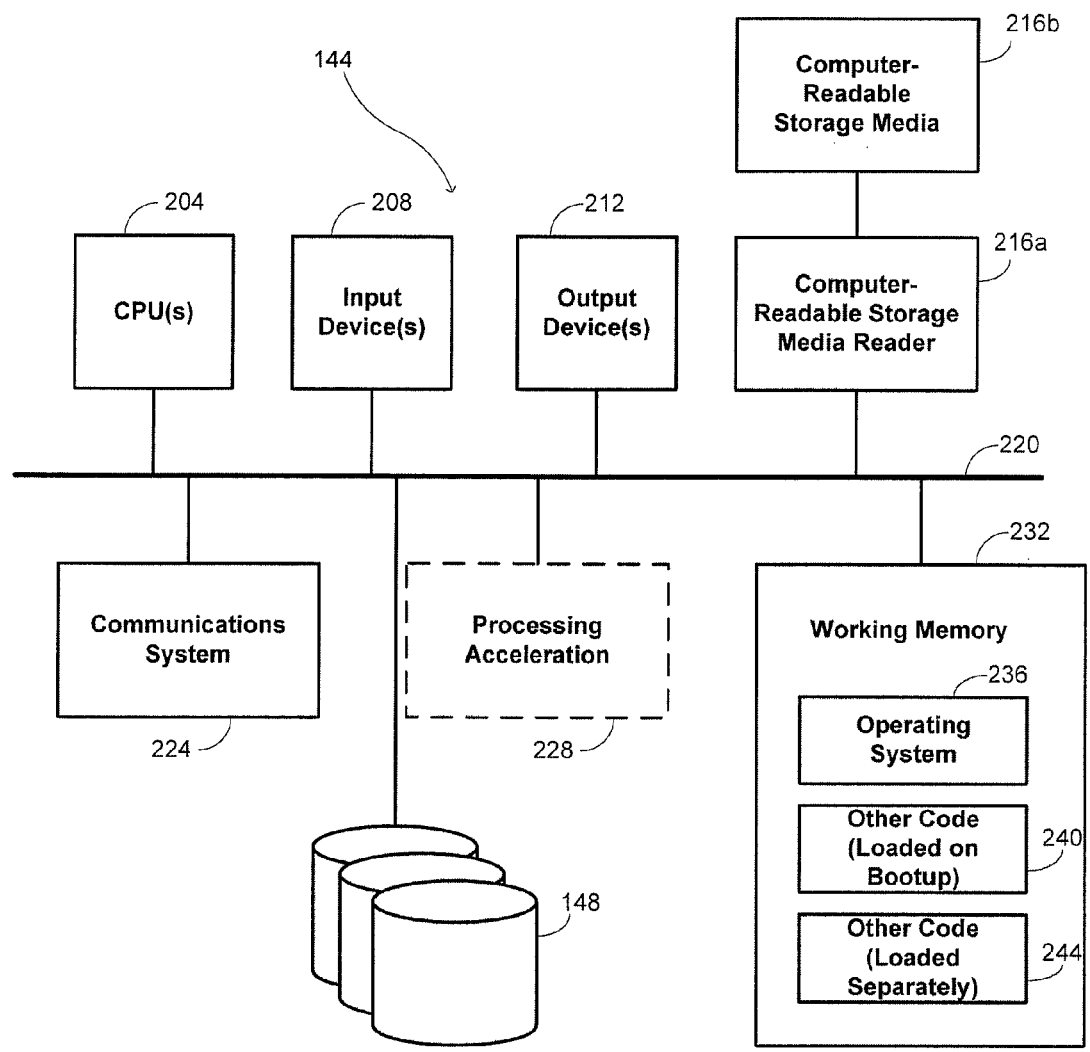
FIG. 2 provides an illustration of a structure that may be used for a remote maintenance system in some embodiments.

FIG. 2 provides a schematic illustration of an embodiment of the maintenance system 144. The drawing broadly illustrates how individual system elements may be implemented in a separated or more integrated manner. The maintenance system 144 is shown comprised of hardware elements that are electrically coupled via bus 220, which also provides for coupling with the database 148. The hardware elements include a processor 204, an input device 208, an output device 212, a computer-readable storage media reader 216*a*, a communications system 224, and a processing acceleration unit 228 such as a digital-signal processor or special-purpose processor. The computer-readable storage media reader 216*a* is further connected to a computer-readable storage medium 216*b*, the combination comprehensively representing remote, local, fixed, and/or removable storage devices plus storage media for temporarily and/or more permanently containing computer-readable information. The communications system 224 may comprise a wired, wireless, modem, and/or other type of interfacing connection and permits data to be exchanged with external devices.

The maintenance system 144 also comprises software elements, shown as being currently located within working memory 232, including an operating system 236 and other code 240 and 244 that may respectively be loaded into working memory on bootup or loaded separately. Such other code may comprise computer programs designed to implement methods of the invention. It will be apparent to those skilled in the art that substantial variations may be used in accordance with specific requirements. For example, customized hardware might also be used and/or particular elements might be implemented in hardware, software (including portable software, such as applets), or both. Further, connection to other computing devices such as network input/output devices may be employed.

A generally similar structure may be used for the diagnostic processor 124, which may be equipped with a local storage device.

Sensors

A number of specific types of sensors that are used in different embodiments are described herein. This description of sensors is not intended to be limiting since many other types of sensors that may be used in lieu of or in addition to those specifically described will be apparent to those of skill in the art.

The internal diagnostic sensors, depicted schematically as circles 112 in FIG. 1, may include voltmeters and ammeters that measure electrical values within the medical imaging device 108 itself. Such sensors may measure the response of particular components as they are successively interrogated, with low voltage values indicating that a particular one of the components is malfunctioning. This is a suitable form of diagnostic, for example, with ultrasound devices that include a large number of acoustic transducers, each of which may be separately interrogated.

Other sensors that are deployed to measure parameters directly from the medical imaging device 108 itself or from components that supply the medical imaging device 108 are denoted with squares 116 in FIG. 1. Such sensors may include sensors that measure additional electrical characteristics. For example, alternating-current ("AC") power-on status may be measured by current sensors mounted on power lines that bring current to the medical imaging device 108. More sophisticated sensors may be deployed to determine low-line and transient quality problems with the input power for the medical imaging device, the power usually being supplied as 3-phase 480V. These power deviations from ideal may affect the operation of the medical imaging device 108 and may be symptomatic of problems either with the power supply or with the device itself depending on how they are manifested.

Medical imaging devices 108 that use a coolant fluid may be monitored with sensors that check the temperature or available volume of the coolant. For instance, sensors may be deployed on water-supply pipes to measure both inlet and outlet temperature of water being supplied to and drawn from the medical imaging device 108. In other embodiments, a water flow sensor may be mounted inline with the cooling water flow to measure the flow rate directly. Similarly, airflow sensors may be deployed to monitor critical airflow for those devices that use air for cooling. Magnetic-resonance devices use liquid He as a coolant, and the volume of available He may be measured by a sensor to give an indication of the remaining level of coolant available.

In addition to measuring the temperature of coolant, temperatures may be measured at other relevant locations using temperature sensors. These include positions proximate an X-ray tube in any of the medical imaging devices 108 that use X rays, including projection-radiograph devices, tomography devices, mammogram devices, and the like. Deviations from an expected temperature may be indicators of a potential malfunction with the device 108. Similarly, temperature sensors deployed on high-power electronic cabinets or components may provide an early warning of overheating of components.

Magnetic field sensors may be used with medical imaging devices 108 that generate magnetic fields, such as magnetic-resonance imaging devices. Such sensors may advantageously be deployed proximate the device 108 at points where magnetic fields are present during normal operation of the device to monitor the overall strength of the magnetic field and variations in the field strength.

Radio-frequency sensors may be mounted on or near X-ray tubes of any medical imaging device 108 that generates X rays as part of its imaging function to detect tube arcing events, which indicate a malfunction with the X-ray generation of the device. Alternatively, acoustic sensors may be used to detect such arcing events by identifying sounds associated with the arcing rather than radio-frequency emissions.

Such acoustic sensing is one example of a broader class of sensors that may be deployed in various configurations to monitor an acoustic signature of the medical imaging device. A properly functioning device will have a characteristic acoustic signature that is recognized by the maintenance system so that deviations from that signature may be used to identify a malfunction or to predict a malfunction. For example, in addition to identifying X-ray tube arcing events, such acoustic sensors may be attached directly to components to sense bearing issues or other abnormal behavior of components such as a rotating anode in an X-ray tube or gantry-rotation issues in tomography systems.

While these are specific examples of events that may be identified from certain sounds, the maintenance system 144 may be configured more generally to recognize deviations from any normal sound pattern produced by the medical imaging device 108. This particularly includes the use of an acoustic ambient sensor mounted on magnetic-resonance-imaging devices to monitor sounds generated by gradient generation. Furthermore, as described more fully below, the maintenance system 144 may include a learning feature in some embodiments that allows it to expand and improve the reliability of anomalous-sound recognition in identifying other types of malfunctions not specifically described.

The evaluation of an acoustic signature need not be limited to sounds that are collected from sensors that are proximate specific components. Instead, acoustic data may be collected more generally from sensors 120 deployed to monitor the ambient medical diagnostic environment 104. Such sensors may monitor the full spectrum of noise emitted by the medical diagnostic device 108, with variations in the noise providing characteristic indications of a component malfunction. For example, the medical diagnostic device 108 may normally give a hum that has certain acoustic properties that change when a fan stops running, when a bearing begins to squeak, or the like.

Other types of environmental sensors 120 include ambient temperature sensors, which may be mounted on a wall within the medical diagnostic environment 104 or elsewhere. Unexpected increases in temperature within a room may indicate that the medical imaging device 108 is overheating and decreases in temperature may indicate that one or more components of the device 108 have stopped functioning.

A humidity sensor mounted on a wall or elsewhere may provide different data, with both unexpected increases in humidity and unexpected decreases indicating potential component malfunctions.

Further examples environmental sensors 120 that may be used in some embodiments include cameras, such as video cameras, still-frame cameras, and/or hyperspectral cameras. Such cameras may monitor the overall medical diagnostic environment 104 to detect abnormal events such as smoke from a failed component. They may also be used in a more direct way to monitor specific components, one example of which is using a camera to monitor the values shown by system gauges that do not have readily accessible sensor signals that can be obtained directly.

Sensors may also be deployed to monitor the emitted electromagnetic or acoustic field from the medical imaging device 108 so that anomalies in the output of the device 108 may be detected. For instance, an X-ray detector array mounted in the path of a systems X-ray beam, such as on a tomography device, allows monitoring of tube X-ray output that can be used to track tube output as a function of various system parameters. This not only improves assessment of tube life, enabling more accurate predictions of when tubes are likely to fail, but also provides a better assessment of patient dose. These benefits are a consequence of the fact that such detectors measure the entire X-ray beam, as compared with system detectors that measure only the uniform center of the X-ray beam. As will be appreciated by those of skill in the art, such detectors may also verify that X-ray collimators are limiting the beam properly. Similar kinds of information may be obtained for other types of medical imaging devices 108 through measurement of an ultrasound field.

Broadly included within the definition of "sensors" herein are a variety of after-sale test equipment provided by third parties, particularly equipment that is configured to test the operation of ultrasound imaging systems and X-ray imaging systems. Examples of such systems include the FirstCall™, FirstAssist™, and OneLook™ available from Unisyn Medical Technologies. Details of some of these technologies is described in the following patents, each of which is incorporated herein by reference in its entirety for all purposes: U.S. Pat. Nos. 7,278,289; 7,155,957; 7,208,529; 7,007,539; 6,928,856; and 6,920,776. Other examples include commercially available x-ray measurement systems, which may similarly be integrated into the system to provide data that are used for maintenance as described herein.

Maintenance

An overview of the maintenance operations according to embodiments of the invention may be understood with reference to FIG. 3, which provides a flow diagram that summarizes how such embodiments may be implemented using the systems described in connection with FIG. 1.

The methods make use of different types of data that may be collected as described above, namely diagnostic data collected from sensors 112 provided as part of the medical imaging device 108 by the original equipment manufacturer, as indicated at block 302; data collected from later deployed sensors 116, as indicated at block 308; and environmental data collected from sensors 120 deployed to monitor the medical imaging environment 104, as indicated at block 312. For each type of sensor, a check may be made respectively at block 316, 320, or 324 whether a parameter measured by the sensor is outside of a predefined range. In many instances, the range is defined by both upper and lower limits, but this is not a requirement and the range may at times be defined only by an upper limit or by a lower limit, with all values less than the upper limit or greater than the lower limit being acceptable without limitation. It will be understood that some of the sensors described above provide data that is directly amenable to such a range check.

For example, sensors that measure such single-value numerical parameters as temperature, humidity, field strength, air or coolant flow rate, etc. provide data that may be evaluated to determine whether the value of the measured parameter falls within the predetermined acceptable range. For such parameters, the database 148 may include a specification of the acceptable range of the parameter. Furthermore, such specifications may at times be universal in the sense that they apply to all medical imaging devices 108, but this is not a requirement. The maintenance system may be configured more flexibly so that different specifications are provided for different types of medical imaging devices 108, varying among such factors as manufacturer, model type, and the like. Such specifications may be derived from info nation provided by the manufacturer of the devices 108 or may be determined independently, particularly if the manufacturer has not specified an appropriate acceptable range for certain parameters that are measured. In some embodiments, though, the specifications may be even more individualized so that, for instance, an acceptable value for humidity is specified for an individual device that is unique to that device, depending on such factors as the physical location of the medical imaging environment 104, past maintenance history of the device 108, and the like.

In other cases, the data are initially collected by the sensor either in a nonquantitative way, such as where cameras are used to monitor the environment, or by collecting multivalue quantitative information, such as where an X-ray field is measured over a range of electromagnetic frequencies. In both cases, the determinations made at blocks 316, 320, and 324 may include processing the collected data to define a single-value parameter that may be determined to be within or outside a limit. For instance, in the case of camera-based monitoring of the medical imaging device 108 to determine whether smoke is present, the image data collected by the sensor may be processed to determine a probability that the image displays smoke by examining such factors as opacity of the environment as seen by the camera. If the probability exceeds a defined value, then the data are determined to be outside a limit at block 324. Similar to evaluation of single-value data, processed nonquantitative and multivalue data may also have ranges defined either universally or more particularly, including specification on a device-by-device basis in some embodiments.

In the case of multivalue data, the processing may take one of many different forms known to those of skill in the art. For example, a spectrum of X-ray energies (frequencies) may be evaluated to determine the maximum or minimum flux at any of the measured enegries, with each of the maximum and minimum being compared with a defined acceptable range—if the flux exceeds the upper limit of the acceptable range at lower energies (soft X rays), then the measured data are determined at block 320 to be outside a limit; similarly, if the flux is less than the lower limit of the acceptable range at high energies, the measured data are also determined to be outside a limit. Other types of processing for multivalue data may include determining a mean value over a range, such as by determining the mean field strength over the measured frequency range, with the data being outside the limit when the mean is outside the limit. A weighted mean may be calculated in other instances, allowing a different level of importance to be applied to different frequency or energy values in the case of X-ray-field measurements, and the like.

The evaluations performed at blocks 316, 320, and 324 may be performed locally by the diagnostic processor 124, which may access stored parameter information over the network 136 from the maintenance system 144, or which may maintain local records of range information and sufficient software to perform the evaluations. Alternatively, the evaluations may be performed by the maintenance system 144 itself, with the diagnostic processor 124 transmitting the collected data to the maintenance system over the network 136.

A determination that measured data, from any of the different kinds of sensors described herein, are outside a defined range may result in the issuance of an alert at block 328. Such alerts may be issued in a variety of different ways in different embodiments. Usually the alert is issued at least to a field service engineer by the maintenance system 144, and in some instances, the alert may additionally be issued to the medical operations center 128. The issuance of an alert may prompt not only the application of maintenance functions described below and coordinated with the maintenance system 144, but may also initiate scheduling changes for use of the medical imaging device 108 by the medical operations center.

Even if all measured data conform acceptably to defined ranges, it is still possible that the maintenance system 144 will issue an alert, but in such cases the alert may have a different character. Alerts prompted by measured data being outside a defined range generally have a more critical status than other types of alerts that may be issued since they generally indicate that a malfunction has already occurred. Other types of alerts, as described below, may be more predictive in nature, providing a basis for conducting repairs for preventive purposes so that a predicted malfunction may be avoided.

Thus, at block 332, sensor data are transmitted to the maintenance system 144 over the network 136 via the diagnostic processor 124 so that the maintenance system 144 can apply predictive modeling to the data. Such predictive modeling is not limited to the evaluation of a single parameter but may also consider correlations among different parameters in light of a maintenance history of the particular medical imaging device 108 or of similar medical imaging devices. The predictive techniques may in this way predict component malfunctions not based solely on how a single parameter changes but on how the combination of multiple parameters is affected by changes in the components that make up the device. In this way, considerably greater information is available from the data that allows those malfunctions to be identified before they actually occur, minimizing the downtime that results from malfunctions and allowing repairs to be scheduled to accommodate schedules when the medical imaging device 108 is planned to be used.

There are multiple ways in which such predictive modeling may be implemented in different embodiments. Correlations between n multiple parameters $X_1, X_2, \ldots X_n$ may be considered through the calculation of correlation functions, where $X_m$ may correspond generally to any or all of the parameters discussed above, with time values of $X_m$ available to the maintenance system over a period of time T divided into discrete moments $t_j$. A correlation function $C_{x_1 x_2 \ldots x_n}$ may be calculated from the parameter values $X_i(t_j)$ at the set of different times $t_j$ in a number of different ways known to those of skill in the art, one example of which is $$C_{x_1 x_2 \ldots x_n} = \frac{\prod_{m=1}^{n} \sum_{j} (X_m(t_j) - \overline{X}_m)}{\prod_{m=1}^{n} \sigma_{x_m}},$$

where the time-averaged mean $\overline{X}_m$ is given by $$\overline{X}_m \equiv \frac{1}{T} \sum_j X_m(t_j)$$

and the time-averaged standard deviation $\sigma_{x_m}$ is given by $$\sigma_{x_m} \equiv \sqrt{\frac{\sum_j (X_m(t_j) - \overline{X}_m)^2}{T}}.$$

The correlation values thus calculated from the received data may thus be subjected to the same kind of analysis described above by examining whether the correlation values deviate from expected ranges, with the degree to which the correlation values deviate being a measure of the likelihood of a predicted failure. In this illustration, each of the correlations have treated the parameters with equal weight, but this may be relaxed in some embodiments so that correlations are calculated with different weight values for parameters derived from different sensors by assigning desired weight values $w_m$ and substituting $X_m(t_j) \rightarrow w_m X_m(t_j)$ in the equations above. The weight values $w_m$ are selected to reflect a determination that the information content associated with a particular sensor is more relevant in identifying certain types of potential malfunctions than some other sensors. The predictive modeling may thus apply different weight values $w_m$ even to the same set of data in evaluating different aspects of operation of the medical imaging device 108. This allows the full data set to be used more fully by exploiting different combinations of information that may yield predictive results.

Figure 4:
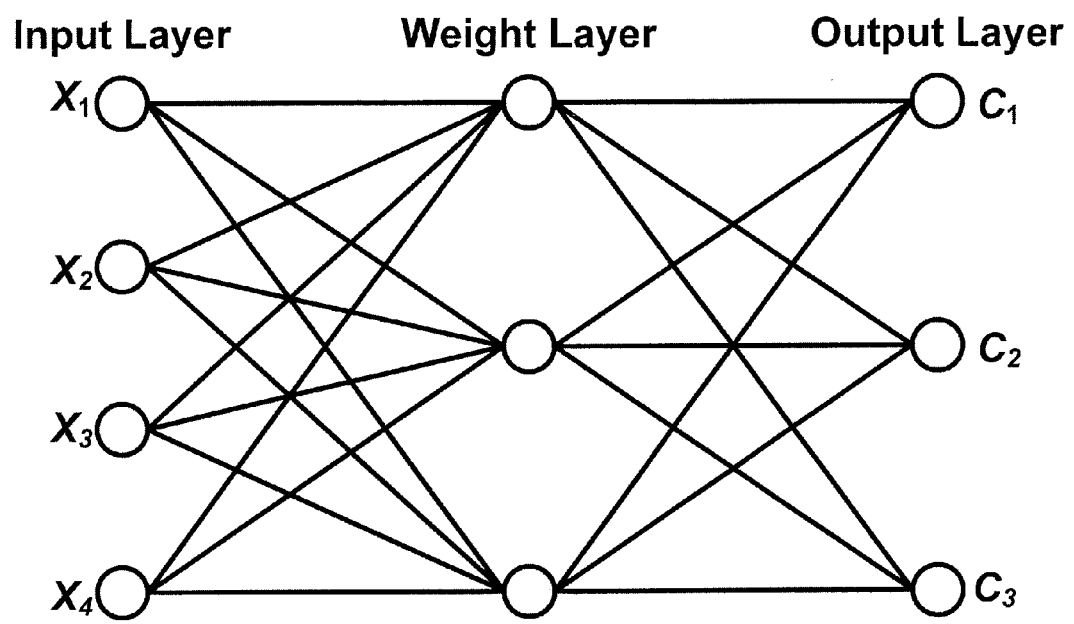
FIG. 4 is a schematic diagram illustrating the structure of a neural net as may be used in certain embodiments.

The appropriate values for the weight values $w_m$ may also be determine in a number of different ways, in some embodiments using techniques that allow for adaptive learning by the maintenance system 144. For example, in some such embodiments, a neural network is implemented by treating the sensor parameters X as inputs and the correlation values C as outputs. A schematic illustration of a structure for a neural network is provided in FIG. 4. In the drawing, the notation for the correlation values has been simplified, with each $C_k$ denoting a correlation value that corresponds to a particular combination of sensor data. A neural network includes a plurality of nodes, each of which has a weight value w associated with it, with the values of the outputs being determined by values of the inputs and by the different weighting factors, shown in the drawing as an intermediate layer in the network. As the maintenance system 144 receives feedback in response to the performance of corrective and maintenance functions on the medical imaging device 108, particularly when incorrect predictions were made, the neural network may reorganize itself to reach the correct decision with the same input data X.

Embodiments of the invention may additionally make use of fuzzy-logic techniques. Fuzzy logic includes a number of techniques that allow decision-making processes to be implemented with inexact information, particularly where ambiguities in the information are nonstatistical in nature. Through the application of fuzzy logic, the information contribution from each of the parameter data sets $X_m$ may be quantified for its relevance to predicting a component malfunction at block 336. Fuzzy logic may generally be viewed as a superset of Boolean logic in which Boolean truth values may be replaced with intermediate degrees of truth. Thus, while Boolean logic allows only for truth values of zero ("false") and one ("true"), fuzzy logic allows for truth values having any real value between zero and one.

Applying fuzzy logic in one embodiment begins by mapping crisp values of the parameter measurements into one or more fuzzy sets. For example, while an alert is issued in response to a parameter having a value outside a defined range as determined at blocks 316, 320, or 324, the actual value of the parameter even when it is within the defined range may nonetheless be suggestive that a malfunction is likely to occur even if it has not yet already occurred. The mapping onto fuzzy sets may map specific parameter values into fuzzy values that indicate a likelihood that a component will fail. If a humidity range is $H_1$ to $H_2$, for example, a value of H within the range may map onto a fuzzy value between 0 and 1 that reflects the fact that the measured humidity H is offset from "ideal." The thus-fuzzified data are acted on by a composition module that maps the fuzzy sets into other fuzzy sets according to combination rules that may be modified with feedback as obtained below. The resulting fuzzy sets are defuzzified to convert them into crisp values from which a decision may be made whether a malfunction is predicted.

The methods of performing predictive modeling described herein are intended to be exemplary. In alternative embodiments, other types of modeling may be used, including the use of expert systems, genetic algorithms, and other techniques.

Figure 3:
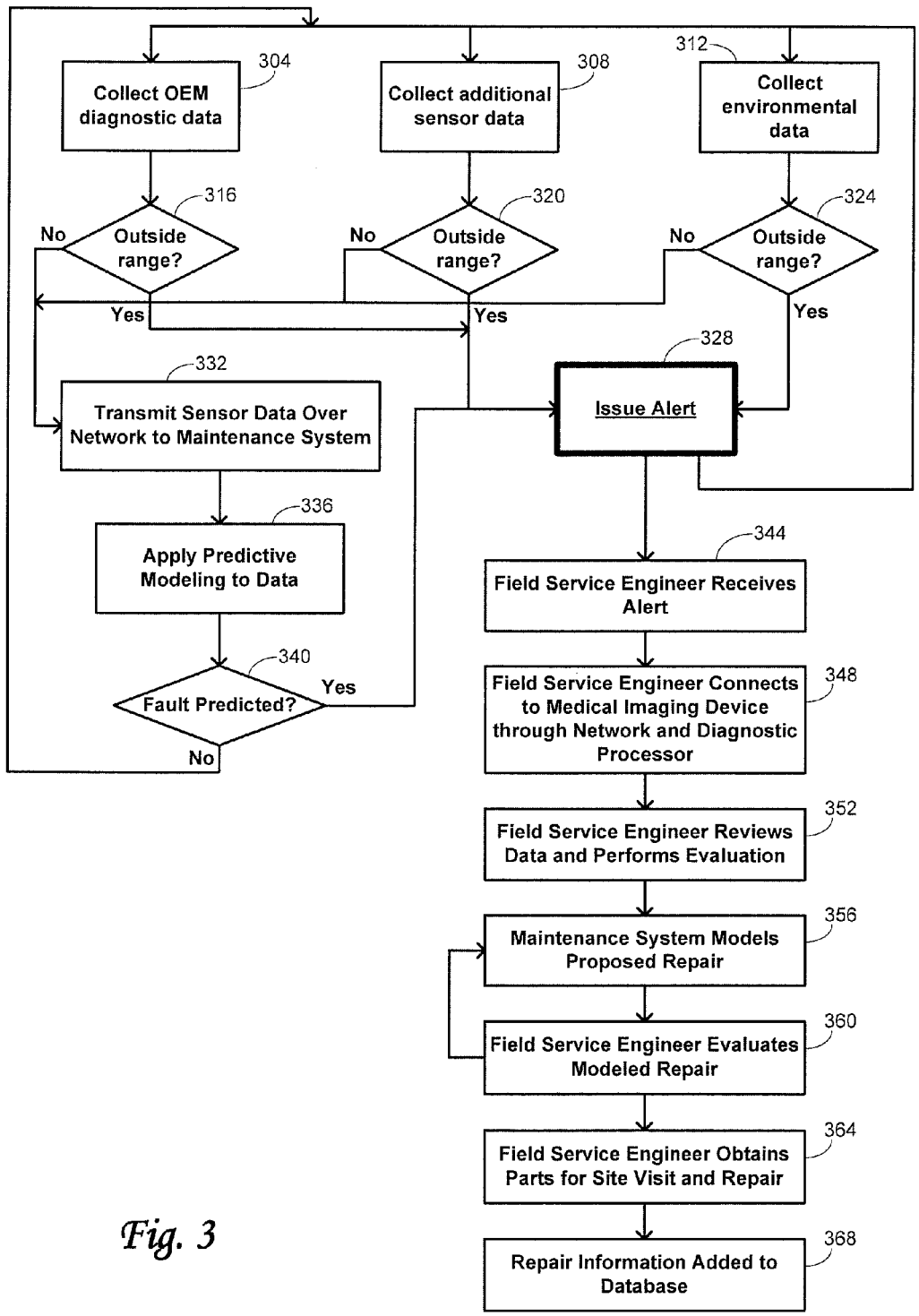
FIG. 3 is a flow diagram that summarizes aspects of methods for providing remote maintenance of medical imaging devices in various embodiments.

After application of the predictive modeling in these or other ways at block 336 of FIG. 3, a decision is made from application of the predictive modeling at block 340 whether a fault is predicted. If so, an alert is issued at block 328, although this alert may be different in character than the alert previously discussed because it does not indicate that a malfunction has actually occurred. As before, the alert is usually issued at least to a field service engineer, as indicated at block 344, but also be directed to the medical operations center 128 in some embodiments.

When the field service engineer receives an alert, whether it is of the first or second types of alerts described above, he or she connects to the medical imaging device through the connections illustrated in FIG. 1, i.e. through the network 136 and the diagnostic processor 124. These connections may be routed through the maintenance system 144, but in some embodiments the field service engineer will connect directly to the network 136. In either case, a web-based interface may be provided to allow the field service engineer to review sensor readings and to interact with both the sensors and with the medical imaging device 108. Access may be limited to authorized field service technicians through access-limitation schemes such as by requiring user and password information, biometric checks, implementation of virtual private networks, and other security systems known to those of skill in the art. With access to the internal functions of the medical imaging device 108, using the functionality of the diagnostic processor 124 to control the medical imaging device 108 remotely in the manner as would be possible if the field service engineer were physically at the device, an evaluation of the sensor data and the basis for the alert may be performed at block 352. As part of servicing the medical imaging device 108 remotely in this way, the field service engineer may use the access provided to download software updates, new diagnostic routines, new diagnostic data, and the like. In addition, the field service engineer may be provided with the ability to alter defined operational ranges of various parameters as a part of providing maintenance and/or repair. Merely by way of example, this might include altering the maximum temperature or humidity accepted as normal by the system, altering acceptable flow-rate settings, and the like. In this way, the maintenance capabilities are enhanced by combining both human and machine evaluations in an adaptive way.

It will be appreciated that access may be provided to the field service engineer using any of a variety of modalities known to those of skill in the art. This includes using email contact, text message or SMS contact, pagers, personal digital assistants, tablet computers, laptops, desktop computers, cellular telephones, and the like. Further, the diagnostic processor 124 may generally be configured to accommodate data formats that may be particular to individual imaging-device manufactures (such as GE, Philips, Siemens, Toshiba, etc.) and to act as an interface for converting those formats to and from a standard format used by the field service engineer in providing maintenance and repair functions. In performing such conversions, appropriate compliance with relevant privacy laws may be implement, such as in embodiments where patient information is stripped from images to avoid noncompliance with HIPAA laws.

The field service engineer's evaluation may be supplemented by interactions with the maintenance system 144 at block 356. In particular, the field service engineer may consider a possible repair and have the maintenance system 144 model the effect of that repair using the other data that have been collected and the maintained information about the medical imaging device 108. The field service engineer evaluates the results of the modeling provided by the maintenance system 144 at block 360. This process of evaluation and modeling may be performed multiple times, with the results of the proposed repair modeling informing decisions of the field service engineer to consider alternative possible repairs and to model those also.

Once the field service engineer has settled on a specific repair, parts may be obtained at block 364 so that the engineer may visit the site of the medical imaging device 108 and effect repairs.

At block 368, information about the repair is added to the database 148. This information may be extensive, and may include such information as the effect that the repair has on the parameters directly measured by the sensors 112, 116, and 120, as well as on any derived parameters produced as part of the modeling. A comparison of predictive modeling before and after the repair, and of the actual effect of the repair as assessed by the field service engineer thus informs the maintenance system 144 whether the predictive modeling was accurate. If inaccurate, the model used in the predictive modeling may be modified, such as by changing the weight factors applied to calculation of correlation functions or as node weighting in a neural net, in mapping crisp parameter values to fuzzy values as described above, or in modifying other types of predictive modeling.

Having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

What is claimed:

1. A method for remotely maintaining a medical imaging device adapted to use electromagnetic or acoustic information to generate an image of at least a portion of a body of a patient, the method comprising:

determining, at a maintenance system disposed remotely from the medical imaging device, a set of operational characteristics for the medical imaging device;

receiving, over a network at the maintenance system, data relating to current operating conditions from a plurality of sensors disposed local to the medical imaging device;

deriving, with the maintenance system, a set of parameter measures from the received data relating to current operating conditions;

analyzing, with the maintenance system, the derived parameter measures by comparing each of the derived parameter measures with a respective normal operating range maintained as part of the set of operational characteristics;

in response to determining that each of the derived parameter measures is within the respective normal operating range, applying predictive modeling to the derived parameters to identify a predicted malfunction of a component of the medical imaging device; and initiating, with the maintenance system, a repair of the medical imaging device by generating an alert in response to identification of the predicted malfunction, wherein the medical imaging device comprises a first medical imaging device manufactured by a first manufacturer, the method further comprising:

maintaining, at the maintenance system, a second set of operational characteristics for a second medical image device adapted to use electromagnetic or acoustic information to generate an image of at least a portion of a body of a second patient, the second medical imaging device being manufactured by a second manufacturer distinct from the first manufacturer and having, at least in part, a design different from a design of the first medical imaging device;

receiving, over the network at the maintenance system, second data from a second plurality of sensors disposed local to the second medical device;

deriving, with the maintenance system, a second set of parameter measures from the received second data;

analyzing, with the maintenance system, the derived second parameter measures in comparison with the second set of operational characteristics to identify a second predicted malfunction of a component of the second medical imaging device; and initiating, with the maintenance system, a repair of the second medical imaging malfunction.

2. The method recited in claim 1 wherein:
at least one of the plurality of sensors comprises a diagnostic sensor provided as part of the medical imaging device by a manufacturer of the medical imaging device; and
at least another of the plurality of sensors comprises a sensor provided separately from the medical imaging device.

3. The method recited in claim 1 wherein at least one of the plurality of sensors collects data associated with a characteristic of an environment within which the medical imaging device is disposed.

4. The method recited in claim 1 wherein:
applying predictive modeling comprises identifying the predicted malfunction from a combination of the derived parameter measures.

5. The method recited in claim 1 wherein:
at least one of the plurality of sensors collects data defining a diagnostic field pattern for an electromagnetic or acoustic field generated by the medical imaging device; and
analyzing the derived parameter measures comprises identifying an anomaly within the diagnostic field pattern.

6. The method recited in claim 1 wherein the medical imaging device is one of a plurality of medical imaging devices disposed remotely from the maintenance system and in communication with the maintenance system.

7. The method recited in claim 1 further comprising:
receiving, at the maintenance system, data related to the repair of the medical imaging device; and
updating the set of operational characteristics in response to the data related to the repair of the medical imaging device.

8. The method recited in claim 1 wherein:
at least one of the sensors comprises a microphone;
the set of parameter measures comprises an acoustic signature of nondiagnostic sounds generated by the medical imaging device; and
analyzing the derived parameter measures comprises identifying an anomaly in the acoustic signature.

9. The method recited in claim 1 further comprising establishing a connection with the medical imaging device with the maintenance system such that a technician may remotely effect changes in the medical imaging device by directing instructions through the maintenance system.

10. The method recited in claim 9 wherein directing instructions through the maintenance system comprises effecting a system reboot of the medical imaging device.

11. The method recited in claim 9 wherein directing instructions through the maintenance system comprises downloading a software update to the medical imaging device.

12. A maintenance system for interfacing with a plurality of sensors disposed to monitor a medical imaging device adapted to use electromagnetic or acoustic information to generate an image of at least a portion of a body of a patient, the maintenance system comprising:
a storage device configured to maintain a set of operational characteristics for the medical imaging device;
a communications device configured to permit exchange of data with the plurality of sensors and with the medical imaging device; and
a processor connected with the storage device and with the communications device, wherein the processor comprises:
instructions to receive, through the communications device, data from the plurality of sensors;
instructions to derive a set of parameter measures from the received data;
instructions to analyze the derived parameters in comparison with the set of operational characteristics to identify a predicted malfunction of a component of the medical imaging device, wherein the instructions to analyze comprise instructions to compare each of the derived parameter measures with a respective normal operating range as part of the set of operational characteristics and instructions to apply predictive modeling, in response to each of the derived parameter measures being within its respective normal operating range; and
instructions to initiate a repair of the medical imaging device by generating an alert in response to identification of the predicted malfunction,
wherein the medical imaging device comprises a first medical imaging device manufactured by a first manufacturer;
the storage device is further configured to maintain a second set of operational characteristics for a second medical imaging device adapted to use electromagnetic or acoustic information to generate an image of at least a portion of a body of a second patient, the second medical imaging device being manufactured by a second manufacturer distinct from the first manufacturer and having, at least in part, a design different from a design of the first medical imaging device;

the communications device is further configured to permit exchange of data with a second plurality of sensors disposed local to the second medical imaging device; and the processor further comprises;

instructions to receive second data from the second plurality of sensors;

instructions to derive a second set of parameter measures from the received second data;

instructions to analyze the derived second parameter measures in comparison with the second set of operational characteristics to identify a second predicted malfunction of a component of the second medical imaging device; and instructions to initiate a repair of the second medical imaging device by malfunction, 13. The maintenance system recited in claim 12 wherein:

at least one of the plurality of sensors comprises a diagnostic sensor provided as part of the medical imaging device by a manufacturer of the medical imaging device; and at least another of the plurality of sensors comprises a sensor provided separately from the medical imaging device.

14. The maintenance system recited in claim 12 wherein at least one of the plurality of sensors collects data associated with a characteristic of an environment within which the medical imaging device is disposed.

15. The maintenance system recited in claim 12 wherein:

the instructions to analyze the derived parameter measures comprise instructions to identify the predicted malfunction from a combination of the derived parameter measures.

16. The maintenance system recited in claim 12 wherein:

at least one of the plurality of sensors collects data defining a diagnostic field pattern for an electromagnetic or acoustic field generated by the medical imaging device; and the instructions to analyze the derived parameter measures comprise instructions to identify an anomaly within the diagnostic field pattern.

17. The maintenance system recited in claim 12 wherein the communications device is in communication with a plurality of remotely disposed medical imaging devices.

18. The maintenance system recited in claim 12 wherein the processor further comprises:

instructions to receive, through the communications device, data related to the repair of the medical imaging device; and instructions to update the set of operational characteristics in response to the data related to the repair of the medical imaging device.

19. The maintenance system recited in claim 12 wherein:

at least one of the sensors comprises a microphone;

the set of parameter measures comprises an acoustic signature of nondiagnostic sounds generated by the medical imaging device; and the instructions to analyze the derived parameter measures comprise instructions to identify an anomaly in the acoustic signature.

20. The maintenance system recited in claim 12 wherein the processor further comprises instructions to establish a connection with the medical imaging device such that a technician may remotely effect changes in the medical imaging device by directing instructions through the maintenance system.

21. The maintenance system recited in claim 20 wherein directing instructions through the maintenance system comprises effecting a system reboot of the medical imaging device.

22. The maintenance system recited in claim 20 wherein directing instructions through the maintenance system comprises downloading a software update to the medical imaging device.

\* \* \* \* \*